United States Patent [19]

Raymond

[11] 4,366,322

[45] Dec. 28, 1982

[54] METHOD FOR THE PRODUCTION OF FURFURAL FROM VEGETABLE MATTER

[75] Inventor: Bernard P. M. Raymond, Ondres, France

[73] Assignee: Bertin & Cie, Plaisir, France

[21] Appl. No.: 253,851

[22] PCT Filed: Jul. 31, 1980

[86] PCT No.: PCT/FR80/00128
§ 371 Date: Apr. 3, 1981
§ 102(e) Date: Apr. 3, 1981

[87] PCT Pub. No.: WO81/00407
PCT Pub. Date: Feb. 19, 1981

[30] Foreign Application Priority Data

Aug. 3, 1979 [FR] France ............................ 79 19935

[51] Int. Cl.³ .......................................... C07D 307/50
[52] U.S. Cl. .................................................. 549/489
[58] Field of Search ................... 260/347.9; 549/489

[56] References Cited

U.S. PATENT DOCUMENTS 1,735,084  11/1929  Miner et al. .................. 260/347.9
4,001,283  1/1977  Wells ............................ 260/347.9

FOREIGN PATENT DOCUMENTS 1493864  10/1972  Fed. Rep. of Germany .

OTHER PUBLICATIONS

Dunlop et al., The Furans, Rheinhold Publishing Corp., New York (1953) pp. 289-295.

Primary Examiner—Richard Raymond
Attorney, Agent, or Firm—Oblon, Fisher, Spivak, McClelland & Maier

[57] ABSTRACT

Process and apparatus for producing furfural from plant materials. The hydrolysis of pentosanes contained in plant materials is effected in a first reactor (2) in the presence of a strong concentrated acid, at 20°–70° C., at atmospheric pressure, and dehydration of the pentoses into furfural is effected in a second reactor (5) by vapor action at atmospheric pressure and at a temperature lower or equal to 110° C., in a strong acid concentrated medium. Application: production of furfural.

19 Claims, 5 Drawing Figures

METHOD FOR THE PRODUCTION OF FURFURAL FROM VEGETABLE MATTER

BACKGROUND OF THE INVENTION

1. Field of the Invention

The present invention relates to a novel process for the preparation of furfural from vegetable matter and to the installation for carrying out this process.

Furfural is a compound of the formula:

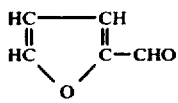

which is of great industrial importance by reason of its numerous applications, notably for the manufacture of synthetic textile fibers, of plastics materials, of synthetic rubbers, etc . . . .

Furfural is obtained from vegetable matter containing pentosans, such as ears of corn, oat, rice or cotton husks, by hydrolysis of the pentosans to obtain pentoses, which by dehydration, give furfural, in accordance with the following reactions:

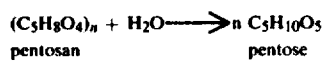 (1)

 (2)

2. Description of the Prior Art

It has been proposed to manufacture furfural from vegetable matter containing pentosans by treatment of the latter, previously moistened with a non-volatile dilute acid, which plays the role of catalyst for the degradation of the pentosans according to the reactions (1) and (2), by steam under relatively high pressure, of the order of 4.2 kg/cm². According to this technique, described in U.S. Pat. No. 1,735,084 of Sept. 7, 1922, treatment with steam under pressure effects at the same time the degradation of the pentosans and the distillation of the furfural resulting from this degradation. However, the yields of furfural obtained by this method are very low, so that the latter only has slight economic interest for the production of furfural on an industrial scale. This is why it has been sought to improve processes for the production of furfural from vegetable matter containing pentosans, by subjecting the latter to steam treatment including essentially two steps, as described in French Pat. No. 1,181,953 of Sept. 3, 1957. According to the process described in this French Patent, the raw material is subjected to a prior treatment with steam, at a pressure close to atmospheric pressure, then to a second treatment step by steam at a higher pressure, varying from 2.8 kg/cm² at the beginning of the operation to 7 kg/cm² at the end of the operation. The non-volatile acid used as catalyst may be sulfuric acid, phosphoric acid or an alkane-sulfonic acid and which can be added to the vegetable matter indifferently either in the second step of the treatment, or in the prior treatment step. The steam utilized in super-heated to about 270° C. at a pressure of 10.5 kg/cm² and the yield of furfural is 68% of theory, which should correspond to about 16% by weight of furfural with respect to the dry weight of the charge. The first step of the process may proceed in a vessel of less robust construction than the digester, which must be adapted to withstand high temperatures and pressures, in which the second step of the process develops. This process however also presents numerous drawbacks, represented by:—the yields of furfural that it provides are still insufficient and—the application of the high temperatures and steam pressures, which necessitate the use, in the course at least of the second step of the process, of special equipment, generally very expensive, adapted to withstand such temperatures and pressures, and have explosion risks.

There also exists a process called "Agrifurane Process" (cf. "TECHNIQUES DE L'INGENIEUR—Genie chimique", Vol 4, page J. 6020-1501) for the production of furfural by hydrolysis in an acid medium of vegetable matter rich in pentosans. This process effects the hydrolysis by the injection of steam into steel reactors under a pressure of 10 bars. The furfuralized vapors which emerge from these reactors contain 5 to 6% by weight of furfural, so that it is necessary, to recover the technical 90% furfural, not only to condense them but to subject them to azeotropic distillation, which is a relatively complicated and expensive operation. The yield of furfural obtained is of 10 to 13% with respect to the dry weight of the raw matter utilized. This process hence has the drawback of applying high pressures, which necessitate the use of reactors resistant to these pressures, and the yield of furfural which it allows to be obtained is extremely low and can only be achieved at the cost of treatments for the removal of the water which involves relatively expensive equipment and which are long and complicated.

It is consequently an object of the present invention to provide an improved process for the production of furfural, which responds better to the necessities of practice than the processes proposed according to the prior art, notably in that it is more economical than the processes of the prior art.

It is another object of the invention to provide a process for the production of furfural which does not have to resort to the application of high temperature and pressures.

It is a further object of the invention to provide a process for the production of furfural which permits the recovery and recycling of the acid used as catalyst.

It is yet another object of the invention to provide a process which enables the yields of furfural production to be improved.

It is yet another object of the invention which provides a process which can be applied with relatively inexpensive equipment, and which does not have to undergo stress imposed by high temperatures and pressures.

Other objects and advantages of the invention will appear from the description which follows.

GENERAL DESCRIPTION OF THE INVENTION

According to the present invention there is provided a process for the production of furfural from vegetable matter containing pentosans, characterised in that in the course of a first step, hydrolysis of the pentosans contained in the vegetable matter is carried out in the presence of a concentrated strong acid, at atmospheric pressure, at a temperature of the order of 20° to 70° C., to obtain a solution of pentoses which is dehydrated in the course of a second step, by the action of steam at a pressure of 1 to 2 bars and at a temperature below or equal to 110° C., in a concentrated acid medium, to give furfural.

According to an advantageous embodiment of the process according to the present invention, the two above steps are carried out in different reactors.

In accordance with the invention, the furfural obtained is subjected to a suitable purification process, to obtain pure furfural.

According to a preferred embodiment of the process according to the invention, the concentrated strong mineral acid in whose presence the hydrolysis of the vegetable matter is carried out is a volatile acid, preferably 5 to 6 N hydrochloric acid (azeotropic concentration at 20% by weight).

According to another preferred embodiment of the invention, the hydrolysis of the vegetable matter by a concentrated strong acid, is carried out within the space of 1 to 2 hours.

When the duration of hydrolysis is limited to 1 to 2 hours, only the pentosans are degraded; if it is prolonged beyond these times, the cellulose of the vegetable matter is attacked by the concentrated strong acid, to give rise to sugars, and notably to glucose.

According to a particularly advantageous modality of the process according to the invention, the hydrolysis process is accelerated by subjecting the reaction medium to stirring.

In accordance with the invention, this stirring is produced by recycling the acid solution of pentoses obtained in the course of the first step, into the reaction medium constituted by the vegetable matter and the concentrated strong acid.

According to another advantageous embodiment of the process according to the invention, the dehydration steam applied in the course of the second step of the process is at a temperature of about 100° to 110° C.

In accordance with the invention, the dehydration step is carried out by counter-current circulation, in a reactor, of the pentose solution to be dehydrated and the dehydration steam.

According to a particularly advantageous feature of the invention, the pentose solution to be dehydrated and the dehydration steam are introduced continuously in the dehydration step.

According to another particularly advantageous feature of the invention, the pentose solution to be dehydrated is admitted at the head of the reactor whence it flows by gravity, whereas the steam circulates in counter-current from the bottom of the reactor, thus permitting rapid continuous extraction, of the furfural formed and avoiding, consequently, any resinification reaction of the latter.

According to yet another advantageous feature of the invention, the pentose solution to be dehydrated is supplemented with a suitable antifoaming agent, which according to an advantageous modality of the invention, may be a silicone based antifoaming agent.

According to another advantageous feature of the invention, at the end of the dehydration step, the concentrated acid is recovered by simple decantation, to be recycled into the hydrolysis step.

According to an advantageous modality of the invention, the acid recovered is subjected, prior to its recycling, to a distillation process to bring it back to its azeotropic composition of 20% by weight.

According to another advantageous feature of the invention, the residue resulting from the hydrolysis of the vegetable matter is separated by simple heating, of the concentrated acid used for the hydrolysis, that it contains, if the latter is a volatile acid, to be recovered and made reusable.

According to another aspect of the present invention there is provided an installation for the production of furfural by applying the above-defined process, which installation is characterised in that it comprises in combination:—at least one first reactor associated with an intake device for the vegetable matter and a concentrated strong acid storage tank to which it is connected by a feed pipe;—at least one second reactor into which opens an inlet pipe for the pentose solution containing the concentrated strong acid, coming from at least one first reactor, and which comprises means for introducing steam at a temperature of the order of 100° to 110° C., a lower orifice for removal of the concentrated acid, which opens into the acid feed pipe of the first reactor and an upper orifice for the removal of the furfuralized steam to a condenser and a decanter whence the liquid furfural separated is sent by suitable means to a storage tank.

According to an advantageous embodiment of the installation according to the invention, at least one first reactor is associated with stirring means for the reaction mixture that it contains and which is essentially constituted by vegetable matter and concentrated strong acid.

According to an advantageous feature of this embodiment, the above said stirring means are constituted by recycling means for the acid solution of pentoses, which recirculate the latter into at least one first reactor.

The introduction of the vegetable matter into such a first reactor, as well as removal of its residue, may be carried out continuously or semi-continuously through lock orifices of known types.

According to another advantageous embodiment of the installation according to the invention, the one or more second reactor(s) is (or are) filled with a packing to improve the distribution and the contact of the reactants in the one or more said second reactor(s).

According to an advantageous feature of the invention, the one or more second reactor(s) is (or are) surrounded with heating means for said one or more reactor(s) such as steam heating coils, for example, to limit the condensation of the dehydration steam to the maximum.

According to an advantageous modality of the invention, the condensed water recovered at the outlet of the condenser and of the decanter, is sent to a boiler or the like whence it is recirculated, after vaporization, in the steam inlet pipe into at least one second reactor.

According to the invention, the boiler or the like is preferably a boiler operating as a thermo-siphon.

According to the invention, the installation comprises in addition a purification installation for the furfural coming from the abovesaid storage tank, in which the furfural is freed from the water that it contains and which is connected, through a pipe to a storage tank for anhydrous furfural.

Also according to the invention, the dehydration acid removed from the one or more second reactor(s) is sent, prior to its recycling into at least one first reactor, into a distillation column to extract therefrom the water (notably the water generated in the course of the reaction) and bring it back to its initial composition).

According to an advantageous feature of the invention, the installation comprises, at the outlet of the at least one first reactor, a condenser-evaporator in which the sugars, and in particular the glucose, obtained by the acid attack of the cellulose of the vegetable matter, are separated from the acid removed from the at least one second reactor, to be recovered at the outlet of said condenser-evaporator, prior to recirculating the acid into the at least one first reactor.

For the practising of the process of furfural production according to the present invention, operation is preferably under the conditions explained below:

The raw material containing the pentosans utilized, is constituted by various vegetable scraps, such as corn cob, husks of oats, of rice, of cotton or other residues of agricultural origin, or by vegetable matter with a rigid structure, such as wood stumps, or again by sawmill scraps such as sawmill ends, shavings, sawdust and wooddust.

The concentrated strong acid applied in the process is, preferably, a volatile acid, such as 5-6 N hydrochloric acid.

The steam utilized in the second step of the process, namely the dehydration step of the pentoses obtained in the first step of the process, is steam at 100°-110° C., at a pressure of 1 to 2 bars, which procures a certain number of advantages, which will be explained below.

The process according to the present invention is applied according to the flow sheet diagram shown in FIG. 1 of the accompanying drawings.

Into the first reactor are introduced the vegetable matter to be treated as well as the concentrated strong acid, preferably volatile, at a temperature comprised between 20° and 70° C. and preferably comprised between 30° and 60° C. The acid hydrolysis reaction of the pentosans of the vegetable matter, is effected in the space of 1 to 2 hours. If the contact time between the acid and the vegetable matter is prolonged, the cellulose of the latter is then attacked by the acid, and is degraded to give sugars, and in particular glucose, which are recovered, by separation of the acid in a suitable installation, prior to recycling the acid into the first reactor: it has been observed that a good yield of glucose is obtained for an average dwell time between the acid and the vegetable matter, of the order of 8 hours.

The hydrolysis of the pentosans gives rise to a pentose solution which is sent into a second reactor, if necessary after passage in a heat exchanger, whilst the residue from the hydrolysis is recovered at the outlet of the first reactor, to be made reusable, after having been treated by heating to free it from the volatile acid which is separated, entraining with it the water possibly contained in the vegetable matter. This residue may be used as fuel, for example to produce the steam necessary for the second step of the process, or as a source of vegetable protein.

The second reactor is advantageously constituted by a column filled with a packing, for example of ceramic, which facilitates the contact and the distribution of the reactants in said reactor.

In certain cases however, a progressive clogging of the packing of this second reactor in which the dehydration takes place occurs, by entrained impurities coming from the vegetable matter treated. In such a case, it is possible to filter the pentose solution by means of a filter mounted on the supply pipe of this second reactor. As a modification, it is possible to replace the packing column by several, three for example, stirred second reactors mounted in series.

As the outlet of the first reactor, the pentose solution containing the concentrated acid is sent to the upper part of the second reactor, whilst the steam at 100°-110° C. is introduced, at a pressure of 1 to 2 bars, and preferably, at atmospheric pressure, at the base of said second reactor. The steam containing furfural is disengaged from the second reactor to be led to a condenser connected to the upper part of said second reactor. The furfuralized steam obtained at the outlet of the second reactor contains 30% of furfural, which constitutes a considerable advantage: in fact, due to the fact that the furfuralization reaction is carried out at atmospheric pressure, the steam which emerges from the furfuralization reactor is more charged with furfural than it could be in a furfuralization treatment which uses a pressure of the order of 10 bars, as is the case in the Agrifurane process. This content of the order of 30% furfural in the steam, enables the furfural to be recovered by a simple condensation and decantation operation and does not necessitate resorting to an azeotropic distillation treatment, difficult to put into operation, with awkward equipment.

After passage into the condenser and into a suitable decanter, the condensed water is sent to a boiler, which operates preferably as a thermo-siphon, in which it is vaporized, then recycled into the steam inlet pipe which feeds the second reactor with steam.

As its outlet from the decanter, the furfural is recovered in the storage tank in the form of 90% furfural, after having been bubbled, as necessary, in a neutralizer containing sodium carbonate and sodium hydroxide to remove therefrom the traces of acid that it contains.

Although reference has been made in the foregoing, to a first reactor in which hydrolysis of the pentosans into pentoses takes place, and to a second reactor in which the dehydration of the pentoses into furfural takes place, it is self-evident that the industrial installation may comprise a plurality of first reactors mounted in series and/or in parallel and a battery of second reactors which are mounted in series and/or in parallel and in which the solution of pentoses and the steam circulate successively in counter-current to improve the distribution and the steam/pentose solution contact and to complete the dehydration reaction of the pentoses into furfural.

The 90% technical furfural may advantageously be subjected to an additional treatment of purification to free it from the water that it still contains at the end of the dehydration treatment, by distillation in a scrubbing column, such as a vacuum plate column, whence the anhydrous furfural is recovered to be sent into a storage tank, whilst the water is recovered and freed, in a condenser and separator, from the traces of furfural that it contains, which are sent to the distillation column, whilst the water may be recovered by any suitable means to be if necessary recycled, after vaporization, into the steam inlet pipe in the second reactor.

The process according to the present invention has numerous advantages with respect to the processes proposed in the prior art.

In fact, the realization of the process in two separate reactors, using moderate temperature conditions and substantially atmospheric pressure, minimizes the side-reactions which are produced in the processes of the prior art at the stage of the dehydration reaction, and notably the resinification of the furfural on its formation, the condensation reactions of the furfural, the oxidation of the furfural by the oxygen contained in the vegetable matter, the risk of these side reactions being practically eliminated not only by the use of conditions of temperature and of pressure according to the invention, but also by the fact that the dehydration of the pentoses takes place in a separate vessel from which the initially treated vegetable matter is absent and that, in addition, the furfural can be separated from the liquid phase, in the form of furfuralized vapor, progressively with its formation, thus avoiding the interfering reactions resulting from prolonged contact between the furfural and the liquid phase.

The use, for the acid hydrolysis, of a concentrated strong acid, enables a good hydrolysis yield to be obtained: it considerably reduces the time of the reaction; moreover, in the dehydration step, the acid is not entrained by the steam and can thus be recycled to the hydrolysis reactor after possible separation of the sugars from the acid. This additional advantage is due to the fact that the dehydration is carried out at 100°–110° C., that is to say at a temperature below the vaporization temperature of the water-concentrated strong acid azeotrope (in the case where hydrochloric acid is used, the vaporization temperature of the water-HCl azeotrope is 110° C.), and that there is a concentration of acid close to the azeotrope: 20% by weight of HCl. To this has been added, as stated above, the use of a volatile concentrated strong acid, such as hydrochloric acid, which considerably facilitates the recovery and making reuse of the residues obtained after hydrolysis since this acid is very easily separated from the solid residue by heating, entraining the water possibly contained in the treated vegetable matter.

The possibility of recycling the acid emerging from the one or more dehydration reactors, represents a very favorable economic factor in the application of the process according to the invention.

In addition, the almost total suppression of the interfering reactions improves considerably, consequently, the yield of furfural obtained.

On the other hand, the flexibility of the process according to the invention, in which it is possible to select at will the time of the acid hydrolysis reaction, enables the composition of the hydrolysate obtained to be controlled and in particular to obtain either only pentoses, or also other useful products such as sugars.

Another advantage of the process according to the invention resides in the fact that the use of moderate temperatures and atmospheric pressure enables the development of the process according to the invention in a relatively inexpensive installation, whereas it has not to be subjected to the stresses resulting from the use of high temperatures and pressures as is the case in the prior art. In addition, the energy investment is considerably reduced with respect to the processes of the prior art due to the fact that operation is at relatively low temperature and at atmospheric pressure, eliminating in addition the risks of heat losses due to the fact of the particularly favorable operational conditions of the process.

In other respects, the safety of the installations is considerably improved with respect to the prior art and, in particular, the risk of explosion is eliminated due to the fact that operation is at atmospheric pressure.

On the other hand, the conditions of application of the process according to the invention enable continuous operation, at the dehydration stage, thus reducing the total duration of the furfural production process with respect to the times necessary in the processes of the prior art.

Another important advantage of the process according to the invention is to remove the need for the azeotropic distillation necessary in the processes of the prior art, since the furfuralized steam which emerges from the furfuralization step contains about 30% of furfural.

In addition to the foregoing features, the invention comprises still other features, which will emerge from the description which follows.

BRIEF DESCRIPTION OF THE DRAWINGS

The invention will be better understood from the additional description which follows, with reference to the accompanying drawings in which.

It must be well understood, however, that these drawings and corresponding descriptive parts, in the same way as the example of practising the process, are given solely by way of illustration of the invention of which they do not constitute a limitation in any way.

DESCRIPTION OF PREFERRED EMBODIMENTS

Figure 1:
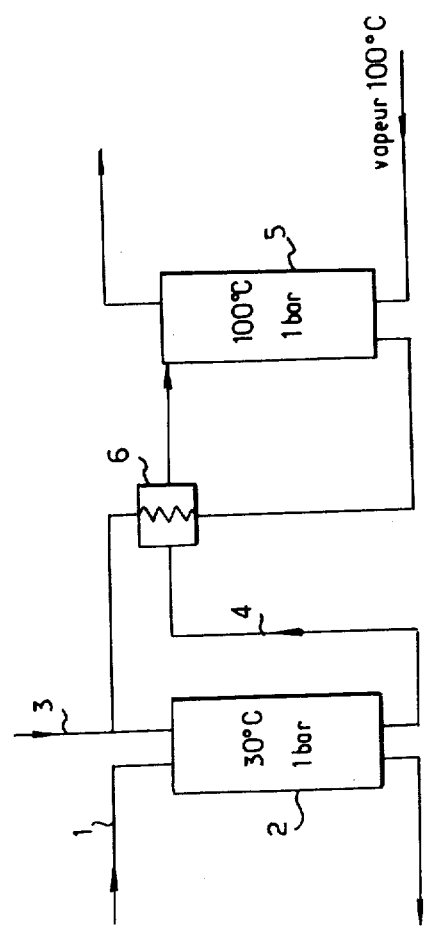
FIG. 1 shows, as already mentioned, the flow diagram of the process according to the invention.

FIG. 1 shows a flow diagram of the process according to the invention, in which the vegetable matter is introduced through a suitable device 1, into a first reactor 2 in which a concentrated strong acid is also introduced through a pipe 3. The concentrated strong acid, which is advantageously 5.5 N hydrochloric acid, at 20% concentration, is introduced into the reactor 2, at a temperature comprised between 20° and 70° C., and preferably, between 30° and 60° C. The hydrolysis takes place in the reactor 2, at atmospheric pressure.

The pentose solution obtained by hydrolysis of the pentosans contained in the vegetable matter treated in the presence of the acid, is sent through the pipe 4 into a second reactor 5, in which it arrives, possibly after reheating in a heater 6. Although the pentose solution containing the concentrated strong acid is introduced at the upper part of the reactor 5, the steam at 100°–110° C. is introduced at the base of the reactor 5, so that a counter-current circulation is established between the pentose solution to be dehydrated and the steam at 100°–110° C. The dehydration reaction of the pentoses takes place substantially at atmospheric pressure at the temperature of the steam, that is to say at 100°–110° C.

The furfural is removed from the reactor 5, preferably at the upper part of the latter, in the form of furfuralised steam which is sent into a condensor, whilst the acid which constitutes the liquid phase, is withdrawn at the base of reactor 5, to be recycled, if necessary after cooling in the exchanger 6, into the hydrolysis reactor 2.

The vegetable residue contained at the end of the hydrolysis of the vegetable matter, is withdrawn from the reactor 2 to undergo heat treatment for removing the residual acid that it contains, with a view to its recovery and reutilisation.

Figure 2:
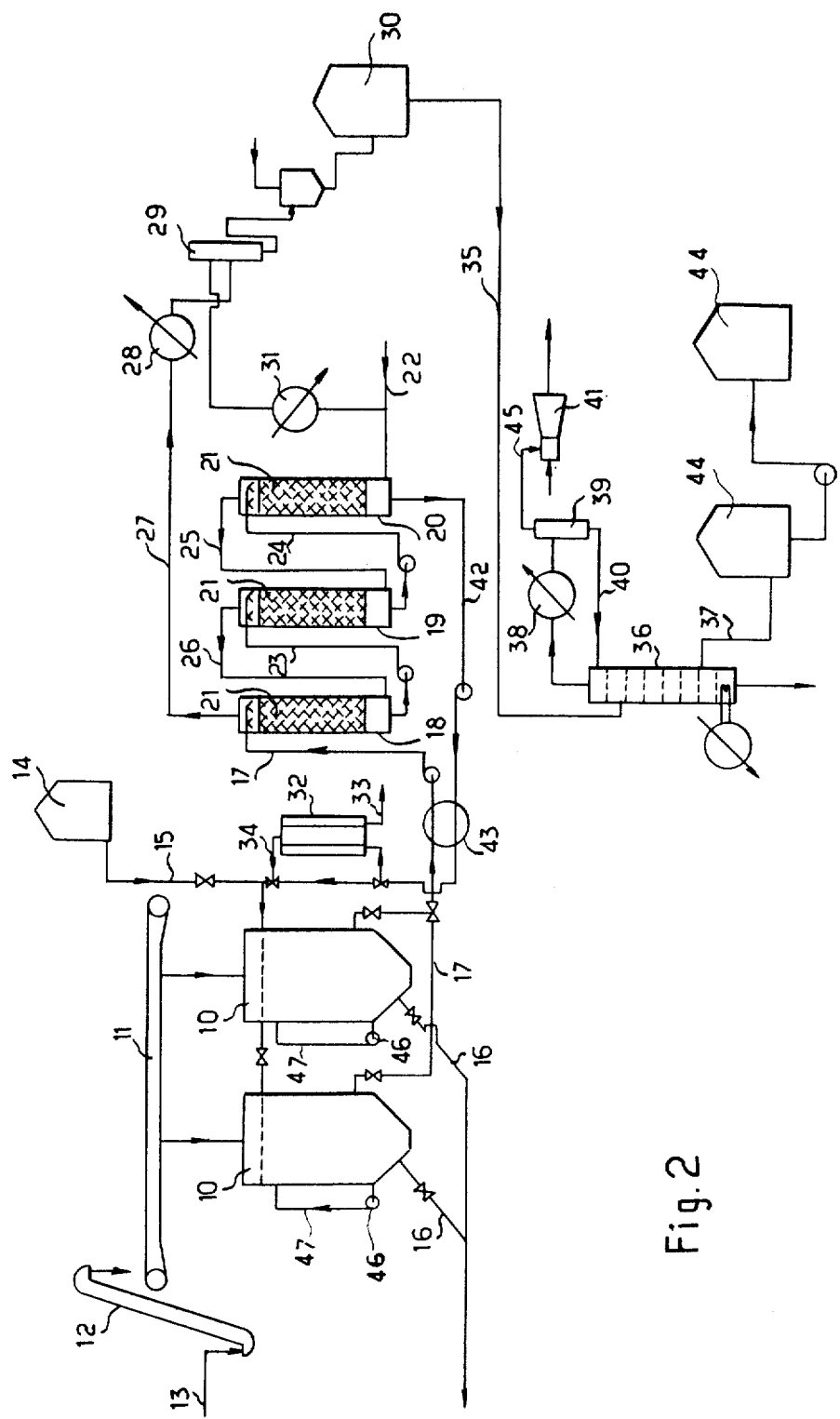
FIG. 2 shows, diagrammatically, one embodiment of a furfural production installation, according to the invention, which refers, in addition, to an example of the practising of the process in an installation according to the invention.

The furfural production installation shown by way of non-limiting example in FIG. 2 is designed according to the flow diagram of operation shown in FIG. 1.

This installation comprises three units:
- a unit in which the hydrolysis of the pentosans into pentoses is effected;
- a unit in which the pentoses are dehydrated to give furfural;
- a scrubbing unit for the technical furfural obtained in the second step, to obtain anhydrous furfural.

The hydrolysis unit comprises two reactors 10 into each of which the vegetable matter to be treated is introduced by means of a suitable device, such as a belt conveyor 11 which cooperates with an elevator or the like 12 which transfers the vegetable matter from the storage location 13 to the conveyor 11. The vegetable matter is advantageously introduced by gravity into the reactors 10.

The concentrated strong acid coming from a storage tank 14 is introduced at a temperature of 20° to 70° C., and preferably at a temperature of 30° to 60° C., into the reactors 10, through the pipe 15. The acid hydrolysis reaction of the pentosans contained in the vegetable matter takes place in the reactors 10, at atmospheric pressure and at a moderate temperature advantageously comprised between 20° and 70° C., and preferably comprised between 30° and 60° C.

Due to the fact of the use of a concentrated strong acid, the hydrolysis reaction is extremely effective and rapid; its duration is on the average from 1 to 2 hours. However, to the extent that it is desired to obtain not only furfural, but also sugars resulting from the attack on the cellulose of the vegetable matter by the acid, it is possible to prolong the time of the reaction in the reactors 10. It appears that a contact time between the vegetable matter and the acid of the order of 8 hours, enables a degradation of the cellulose to glucose to be produced, which is recovered as will be explained below. The duration of the hydrolysis reaction is also determined by the type of vegetable matter treated: thus its duration will be longer in the case where vegetable matter with a rigid structure is processed, such as wood stumps, for example.

At the outlet of the reactors 10, are collected, on the one hand vegetable residue from the hydrolysis which is withdrawn through pipes 16 and, on the other hand, the pentose solution containing the concentrated strong acid. In the case where not only the hydrolysis of the pentosans is carried out, but also the degradation of the cellulose into sugars, and notably into glucose, it is necessary to provide a separating installation for the sugars from the attacking acid, which installation may advantageously be constituted by an evaporator-condensor 32 mounted in by-pass on the pipe 42, at the outlet of which the sugars, notably the glucose, are recovered (at 33), whilst the acid is recirculated through the pipe 34, into the pipe 15 for supplying the reactors 10 with acid.

The hydrolysis reaction is accelerated in the reactors 10 by subjecting the reaction medium, constituted by the vegetable matter and the acid, to stirring. This stirring is advantageously produced by recirculation of the acid pentose solution obtained in the reaction medium: all or part of said solution is taken up again by a pump 46 and recycled into each of the reactors 10 through a pipe 47.

The pentose solution containing the concentrated strong acid is sent, if necessary after bringing to suitable temperature in a heat exchanger 43, through a pipe 17 into a battery of columns 18, 19, 20 mounted in series, containing a contact packing 21, of ceramic, for example.

Steam at 100°–110° C. is also sent through a pipe 22 into the battery of columns 18, 19, 20. Whereas the pentose solution is introduced successively at the upper part of the columns 18, 19, 20 through pipes 17, 23 and 24, the steam at 100°–110° C. is introduced at atmospheric pressure at the base of the column 20, in which it circulates in counter-current to the pentose solution; it thus converts the pentoses by dehydration into furfural which it entrains on its passage successively in the columns, namely 19 through the pipe 25, and 18 through the pipe 26: the furfuralised steam is removed at the top of the column 18 through a pipe 27; these furfuralised vapors contain 30% of furfural due to the fact that the treatment is carried out at atmospheric pressure, thus enabling the vapors to receive a greater charge of furfural than is the case in processing installation of the prior art, in which the pressure applied, which is generally of the order of 10 bars, prevents the vapors from being charged with furfural to a proportion higher than 5 to 6%. Due to the fact of their high content of furfural, the furfuralised vapors do not have to undergo, to enable the recovery of the furfural, an azeotropic distillation treatment as is the case in the prior art; a simple treatment by passage in a condensor 28, and then a decantor 29, suffices to recover the liquid furfural; the liquid furfural, decanted in the decanter 29, is sent to a storage tank 30 if necessary after neutralisation, the condensed water being sent from the decanter 29 into a boilor 31 where it is vaporised to be recycled in the pipe 22 for supplying the column 20 with steam at 100°–110° C. The hydrochloric acid is withdrawn at the base of the column 20 whence it is recycled through the pipe 42 into the pipe 15 for supplying the reactors 10 with acid, after having been cooled to a temperature of 20°–70° C. and preferably to 30°–60° C. in a heat exchanger 43 and after being freed from the sugars that it contains, in the evaporator-condenser 32, as indicated above.

The furfural collected in the tank 30 is a 90% technical furfural from which it is necessary to eliminate the water present as impurity, to the extent that it is desired to obtain anhydrous furfural. This purification step is carried out by circulation of the 90% technical furfural solution into a purification installation known in itself, such as a plate distillation column 37. The furfural is introduced through the pipe 35 into said column at about 50° C., under a vacuum of 0.1 bar. The anhydrous furfural obtained is withdrawn through a pipe 37 to be sent to storage tanks 44, whilst the water separated from the furfural and containing a small amount of dissolved furfural is sent into a condenser 38, then a separator 39 whence the decanted furfural is sent back into the column 36 through a pipe 40, whilst the water is removed, through a pipe 45, to an ejector 41 which sends it, if necessary, by any suitable means to the boiler 31 where it is vaporised, and then recycled into the pipe 22.

EXAMPLE OF THE PRACTISING OF THE FURFURAL PRODUCTION PROCESS ACCORDING TO THE INVENTION

Corn cobs with 12% of moisture are introduced at the rate of 1.95 ton/hour into each of the reactors 10, by means of the belt conveyer 11. The 5.5 N hydrochloric acid at 20% azeotropic concentration at a temperature of 40° C., coming from the tank 14, is introduced through the pipe 15 into each of the reactors 10.

The duration of the acid hydrolysis, which is carried out in the reactors 10 at a pressure of 1 bar and at a temperature of 40° C., is about 8 hours. The duration of hydrolysis of the pentosans contained in the vegetable matter into pentoses is only 1 hour, under the conditions of the reaction. The prolongation of the contact time of the vegetable matter with the hydrochloric acid used as hydrolysis catalyst, up to 8 hours, causes the attack of the cellulose of the vegetable matter and its degredation to the stage of glucose. The pentose solution obtained which contains hydrochloric acid and glucose is recycled at least in part by means of the pump 46 and the pipe 47 to each of the reactors 10, to cause stirring in the reactor and accelerate on the one hand the hydrolysis and on the other hand the degradation of the cellulose. The solution of pentoses which contains the hydrochloric acid, leaves the reactors 10 through the pipe 17 to the furfuralisation step. The vegetable residue from the hydrolysis is withdrawn from the reactors 10 through the pipe 16, at the rate of 1.45 ton/hour, to suitable processing units.

The acid solution of pentoses is sent, through the pipe 17, into a battery of packed columns 18, 19, 20 at the same time as the steam at 105° C. and at a pressure of 1 to 1.3 bars, is introduced in counter-current in the battery of columns 20, 19, 18.

At their outlet from the battery of columns 18, 19, 20, the furfuralized vapors at 100° C., containing 30% of furfural, are treated in a condenser, then in a decanter to recover the 90% technical furfural and the water which is vaporized and recycled in the form of steam into the battery of columns 20, 19, 18.

The hydrochloric acid is withdrawn, at the rate of 13 m³/hour, at the base of the column 20 to be recycled into the circuit 15 supplying acid to the reactors 10, if necessary after restoring to the temperature of 40° C. in the exchanger 43. Before being recycled into the acid supply circuit 15 of the reactors 10, the hydrochloric acid from the pipe 42 is sent, through a branch line, into an evaporator-condenser 32 in which it is freed from the glucose that it contains, which is recovered at 33, for its use and/or possible rendering of commercial value.

Anhydrous furfural at the rate of 250 kg/hour is obtained by treatment of a 90% technical furfural obtained at the outlet from the dehydration stage, in a vacuum purification installation (0.1 bar) at 50° C. comprising essentially a plate distillation column or the like as described above with respect to FIG. 2.

Figure 3:
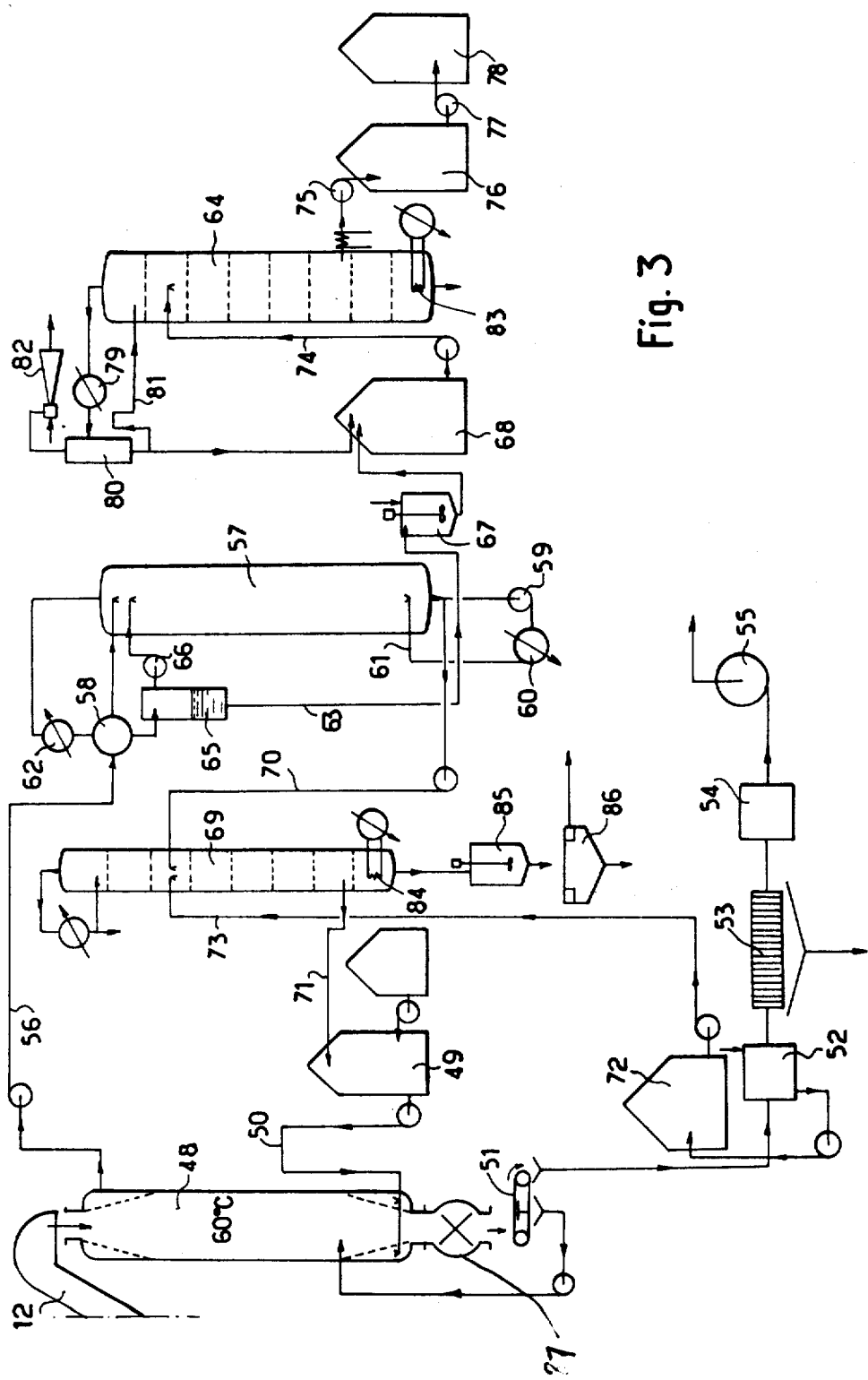
FIG. 3 shows, diagrammatically, another embodiment of a furfural production installation, according to the invention.

The furfural production installation shown by way of non-limiting example in FIG. 3 is designed, in the same way as the installation in FIG. 2, according to the operating flow diagram shown in FIG. 1.

In the installation of FIG. 3, the unit in which the hydrolysis of the pentosans into pentoses is carried out comprises a single reactor 48, in which the vegetable matter to be treated is introduced continuously by means of a suitable device such as that described with reference to FIG. 2.

The concentrated strong acid coming from a storage tank 49 is introduced continuously at a temperature of 60° C., into the reactor 48 through the pipe 50, in counter-current to the vegetable matter. The acid hydrolysis reaction of the pentosans contained in the vegetable matter takes place in the reactor 48, at atmospheric pressure and at a moderate temperature, of the order of 60° C., in the space of 1 to 20 hours. The vegetable residue from the hydrolysis, is collected, at the base of the reactor 48, through a reaction lock chamber 87 for example, on a band filter 51, where it undergoes draining, and whence it is sent into a water washing column 52, to extract the acid therefrom; then it is transferred into a screw press 53 in which it is dehydrated before being burnt and gasified in a burner kiln 54 to provide steam, stored in the container 55, designed to be used for the furfuralization.

The pentose solution containing the concentrated strong acid is collected at the head of the reactor 48 and is sent through the pipe 56 into a furfuralization reactor 57, after having been brought to suitable temperature in a heat exchanger 58, and if necessary supplemented with an antifoaming agent. The furfuralization column 57 may if necessary contain a contact packing of suitable material. Steam at 110° C. is introduced into the base of the furfuralization column 57, in counter-current with the pentose solution to be converted into furfural, under a pressure of 1.3 bars. Rather than introduce the steam directly into the column 57, as in the embodiment shown in FIG. 2, in the installation shown diagrammatically in FIG. 3, the solution, run by gravity to the base of the column 57, is recirculated, by means of a pump 59 into a thermo-siphon boiler 60 in which a part of the liquid is vaporized, the steam formed being injected through the pipe 61 to the base of the column 57.

The furfuralized steam emerges at the head of the column with 30% by weight of furfural. After condensation and cooling in the condenser 62, the water-furfural mixture is separated into two phases in the separator 65:

- a phase with 95% by weight of furfural which is sent, through the pipe 63, into the dehydration column 64;
- a phase with 8% by weight of furfural which is reinjected by means of the pump 66 into the furfuralization column 57.

Preferably, the phase with 95% by weight of furfural is subjected, before being introduced into the dehydration column 64, to a neutralization process, preferably by means of $Na_2CO_3$, in a reactor 67 whence it is withdrawn into the vat 68.

The concentrated strong acid is withdrawn at the base of the furfuralization column 57 for recycling into the hydrolysis reactor 48. However, taking into account the residual moisture of the vegetable matter treated by the acid in the reactor 48 and the water generated in the course of the furfuralization reaction, the titer of acid has a tendency to be below its initial composition, at the outlet of the column 57. It is hence opportune to bring back the acid to its initial titer before recycling it into the reactor 48. Such rectification is carried out in a distillation column 69 into which the dilute acid withdrawn from the column 57 is led through the pipe 70. There is collected:

- at the head of the column 69 the residual water and the possible volatile substances entrained by the acid at the outlet of the column 57 (such as methanol)

at the bottom of the column 69, the rectified acid ready to be recycled into the reactor 48 through the pipe 71 (by passing through the storage tank 49 and the pipe 50).

The distillation column 69 processes not only the acid withdrawn at its outlet from the furfuralization column 64, but advantageously also the acid extracted from the vegetable residue at its outlet from the reactor 48, which is brought to it through the pipe 73 coming from the tank 72.

The phase with 95% by weight of furfural is introduced, through the pipe 74, into the dehydration column 64 which operates under a vacuum of 100 mm Hg, at 100° C. The column 64 is a plate distillation column in which the furfural coming from the furfuralization column, which is a 95% technical furfural, is dehydrated to remove therefrom the water present as impurity. The 99% furfural obtained at the outlet of the distillation column 64 is removed from the latter by means of the pump 75, to be sent into the receiving vat 76 then, by means of the pump 77 into the anhydrous furfural storage vat 78.

The water separated from the furfural and containing a small amount of dissolved furfural, is removed at the head of the distillation column 64 to be sent into a condenser 79, then a separator 80 whence the decanted furfural is sent back into the column 64 through the pipe 81, whilst the water is removed to an ejector 82 from which it can be sent into the thermo-siphon boiler 60 where it is vaporized, then recycled into the furfuralization column 57.

Just as the vegetable residue from the hydrolysis is incinerated to provide steam for the furfuralization step, thus rendering the process autonomous in energy, the impurities withdrawn at the foot (83) of the furfuralization column 57 are also sent to the incinerator 54 to be burnt and provide the steam useful in the process, and the impurities coming from the hydrolysis of the vegetable matter recovered at the foot of the column 69 for regenerating the concentrated strong acid of hydrolysis are sent, after neutralization in the reactor 85 and separation in the decanter 86, to the incinerator 54 where they are also burnt to provide steam to the process.

There will be described below, by way of non-limiting example the application of the installation shown diagrammatically in FIG. 3, to the production of 5000 t/year of furfural, from 35,000 t/year of corn cobs with 30% moisture (it being however understood that the process according to the invention applies with the same advantages to the production of furfural from vegetable matter rich in pentosans, with a lesser moisture content), the weight of dry matter being hence of the order of 25,000 t/year and its composition being:

32% of pentosans
50% of cellulose
18% of lignin.

The hydrolyser 48 whose volume is 40 m$^3$ is supplied with corn cobs at the rate of about 3.12 t/hour of dry matter and with 20% hydrochloric acid at 60° C., at the rate of 9.36 m$^3$/hour. The flow rate of the hydrolysate solution at the outlet 56 of the hydrolyser 48 is 6.55 m$^3$/hour and the concentration of pentoses of the hydrolysate is 150 g/liter.

The hydrolysate solution containing 150 g/liter of pentoses enters the furfuralization column 57 whose useful volume is 14 m$^3$ at a flow rate of 6.55 m$^3$/hour. The steam is injected at 110° C., at a pressure of 1.3 bars, at a flow rate of 1.5 t/hour. The furfuralized steam which emerges from the column 57 is condensed in the condenser 62 to give notably a water-furfural mixture with 95% by weight of furfural (and a concentration of pentoses of 8 g/liter). Under these conditions, the flow rate of the recycling pump 59 into the boiler 60 is 27 m$^3$/hour.

The regeneration of the hydrolysis acid, such as hydrochloric acid, at the outlet of the furfuralization column 57 and prior to its recycling into the hydrolyser 48, is carried out in the distillation column 69, which is preferably a plate column. The column 69 is supplied by a hydrochloric acid solution coming:

from the extraction of the vegetable residue at its outlet from the hydrolyser 48, collected in the tank 72: 3.46 T/hour with 13% HCl from the furfuralization: 8.56 T/hour with 17% HCl namely, in total, 11.7 T/hour with 15.8% HCl by weight, with a supply flow rate of 12 T/hour at 14.8% of HCl by weight. The withdrawal flow rate of the HCl regenerated at the bottom of the column is 9.3 T/hour of HCl at 20% azeotropic concentration.

The outlet flow rate of the residual water at the head of the column is 2.42 T/hour and the impurities flow rate at the foot of the column is 0.3 T/hour.

The HCl loss is 1% with respect to the supply HCl, namely, on a 5,000 T/year furfural unit, at the furfuralization level: 1.4×0.01=0.014 T/hour of HCl at the level of withdrawal of the impurities: 0.3 T/hour×0.2=0.06 T/hour of HCL, namely 0.4 T/T of furfural.

The mixture with 95% by weight of furfural is sent after decantation into the decanter 65 and neutralization into the reactor 67, at a supply flow rate of 0.67 T/hour, into a dehydration column 64 which operates under a vacuum of 100 mm Hg, to obtain at the outlet of the column 64, a 99% by weight furfural, with an outlet flow rate of 0.65 T/hour, after having extracted about 0.04 T/hour of water. The 99% furfural is obtained at the rate of 625 kg/hour.

The total consumption of the installation in steam is 7 T/hour and the total consumption of water 185 m$^3$/hour.

The combustion of the 2.12 T/hour (in dry matter) of vegetable residue coming from the hydrolyser 48—with a PCI of 3,400 kcal/kg—produces 7,200 Th/h, namely 11 T/hour of steam, which is hence supplied in large excess with respect to the requirements of the installation (about 7 T/hour).

The influence of temperature on the kinetics of the hydrolysis reaction of the pentosans into pentoses has been determined by studying the development of pentose in the closed hydrolysis reactor, as a function of the times for several temperatures.

The conditions of these tests are assembled in Table I below:

TABLE I

TESTS OF THE HYDROLYSIS OF VEGETABLE MATTER RICH IN PENTOSANS INTO PENTOSES

Cobs used: corn cobs dried in Crib - composition: 11% moisture by weight
38% of pentosans by weight
- density: 160 kg/m$^3$

| Test no. | Temperature (C.) | Weight of crude cobs in the hydrolyser (kg) | Weight of dry matter (kg) | Weight of pentosans (kg) | Volume of 20% acid in the hydrolyser (l) | Total liquid volume (l) | Maximum concentration of pentoses in the hydrolyser (g/l) | Weight of dry matter / Liquid weight |
|---|---|---|---|---|---|---|---|---|
| 1 | 23 | 45.6 | 40.5 | 15.4 | 173 | 178 | 99 | 0.26 |
| 2 | 47 | 40.4 | 36 | 13.6 | 150 | 154.4 | 100 | 0.27 |
| 3 | 60 | 40 | 35.6 | 13.5 | 175 | 179.4 | 85 | 0.22 |

Figure 4:
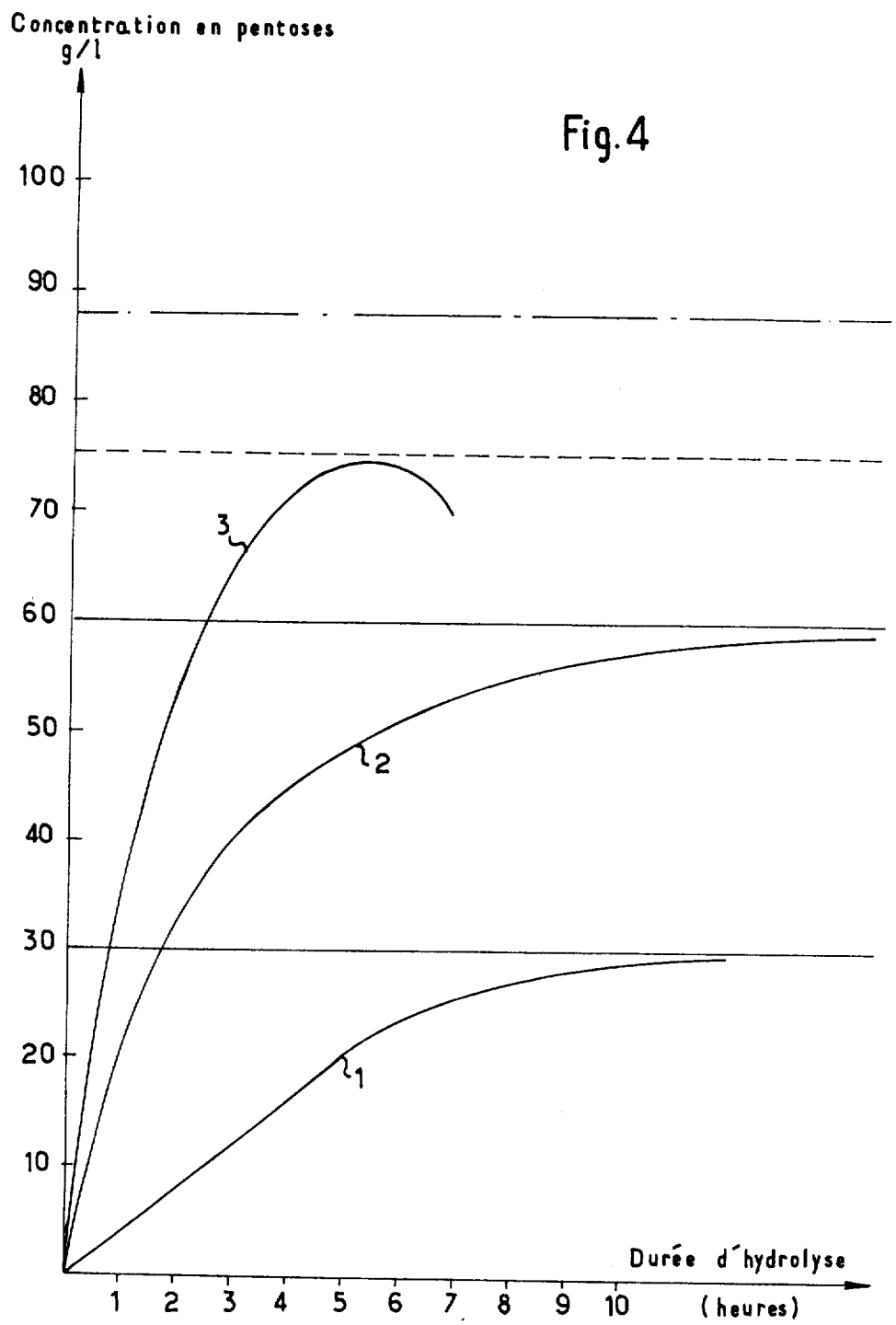
FIG. 4 shows in the form of graphs the influence of temperature on the kinetics of the hydrolysis reaction, whilst

The change in concentration of pentose in the hydrolyser as a function of temperature, emerges from the graphs of FIG. 4 in which:

graph (1) shows the development at 23° C.
graph (2) shows the development at 47° C.
graph (3) shows the development at 60° C.

These tests permit two phenomena to be demonstrated:

the appearance of a pentosan-pentose equilibrium which slows down the hydrolysis kinetics and which prevents the maximum concentration of pentoses to be reached in the closed reactor, the appearance of a degradation reaction for the temperature of 60° C. and a duration of hydrolysis of about 5 hours and enable the enthalpy of the hydrolysis reaction to be calculated:

$$\Delta H = 15.5k \text{ cal/mol}$$

Figure 5:
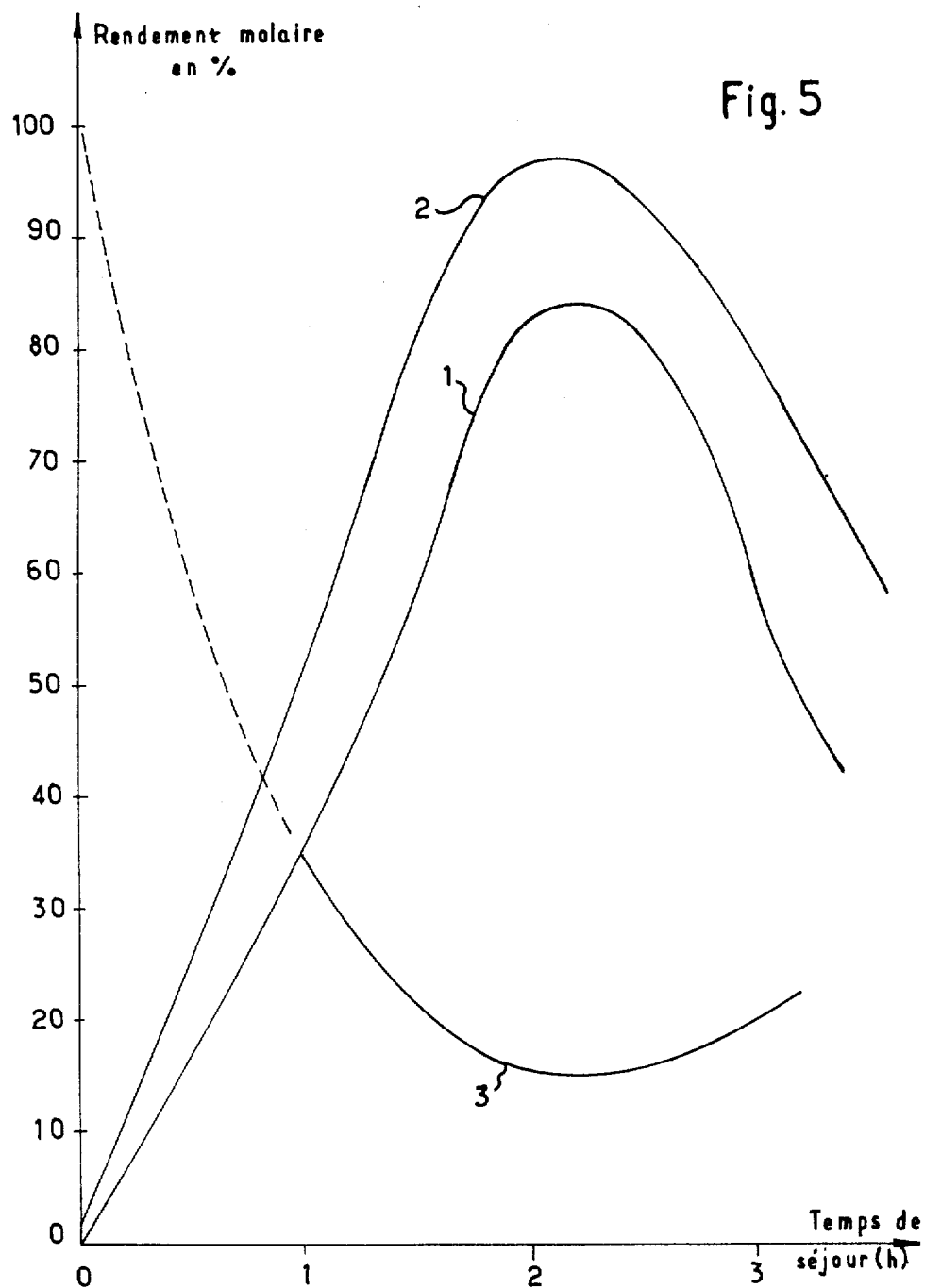
FIG. 5 shows the graphs of the molar yields of the furfuralisation reaction.

Study of the influence of the dwell time of the hydrolysate in the furfuralization column on the yield of furfural has given the following results, which have been translated into graphs in the accompanying FIG. 5:

the yield of furfural increases as a function of the dwell time in the furfuralization column. The optimum is obtained when the dwell time is adapted to the kinetics for the production of the furfural: cf. graph (1) of FIG. 5 where dt=2 hours;

the yield of furfural decreases for high dwell times (dt>2 hours); the interfering reactions are no longer negligible.

The graph 2 gives the molar yield furfural+pentose obtained per mole of pentose injected and the graph 3 gives the level of pentoses unconverted into furfural. These graphs enable the excellent yield of furfural which can be reached by the process according to the present invention, to be verified.

It results from the foregoing description that, whatever the modes of practising, the embodiments and applications adopted, processes and installations for the production of furfural from vegetable matter are provided, having with respect to earlier processes and installations for the same purpose, important advantages of which certain have been mentioned in the foregoing and which others will emerge from the utilization of said processes and installations.

Thus as emerges from the foregoing, the invention is in no way limited to those of its methods of practice, embodiments and applications which have just been described more explicitly; it encompasses on the contrary all modifications which may come to the spirit of the technician in the art, without departing from the scope, nor the spirit, of the present invention.

I claim:

1. A process for the production of furfural from vegetable material containing pentosans, comprising:
    (a) in a first reactor, hydrolyzing pentosans present in said vegetable matter in the presence of a concentrated strong acid at or near atmospheric pressure at a temperature of about 20° to 70° C., thereby obtaining a solution of pentosis; and (b) in a second reactor, dehydrating said solution of pentoses by the action of steam applied at a pressure of about 1 to 2 bars absolute and at a temperature up to 110° C. in a concentrated acid medium, thereby yielding furfural.

2. The process of claim 1, wherein said concentrated strong acid in said first reactor is a volatile acid.

3. The process of claim 1, wherein said volatile concentrated strong acid is 5 to 6 N hydrochloric acid at 20% by weight azeotropic concentration.

4. The process of claim 1, wherein the hydrolysis of the vegetable matter with the concentrated strong acid is conducted within the period of 1 to 2 hours.

5. The process of claim 1, wherein the contact time between the vegetable matter and the concentrated strong acid is prolonged up to 4 to 12 hours, thereby causing degradation of the cellulose of the vegetable matter to sugars, notably glucose, which are recovered.

6. The process of claim 1, wherein the hydrolysis step is accelerated by subjecting the reaction medium to stirring.

7. The process of claim 6, wherein the reaction medium containing said vegetable matter and the concentrated strong acid is stirred by recycling the acid pentose solution obtained from said first step.

8. The process of claim 1, wherein said steam is injected into said second reactor during the dehydration reaction at a temperature of about 100° to 110° C.

9. The process of claim 1, wherein the dehydration step is conducted by counter-current circulation, in said second reactor, of the pentose solution to be dehydrated and said steam.

10. The process of claim 9, wherein the pentose solution to be dehydrated and said steam are introduced continuously into said second reactor.

11. The process of claim 10, wherein the pentose solution to be dehydrated is admitted at the head of said second reactor from whence it flows downwardly by gravity, while the steam circulates counter-currently from the bottom of the reactor, thus enabling rapid continuous extraction of the furfural formed, and avoiding consequently, any resinification reaction of said furfural.

12. The process of claim 9, wherein said steam introduced into the dehydration step is obtained by the combustion and gasification of vegetable residue obtained from the hydrolysis step.

13. The process according to claim 9, wherein said steam introduced into the dehydration step is obtained by vaporization of a portion of the pentose solution introduced into the dehydration step.

14. The process of claim 1, wherein the pentose solution to be dehydrated is supplemented with an antifoaming agent.

15. The process of claim 1, wherein, at the end of the dehydration step, the concentrated acid is recovered by simple decantation and recycled to the hydrolysis step.

16. The process of claim 1, wherein the acid recovered at the end of the dehydration step is subjected, prior to its recycling, to distillation in order to adjust its concentration to a 20% by weight azeotropic composition.

17. The process of claim 1, wherein the residue resulting from the hydrolysis of the vegetable matter is separated by heating said residue to recover said acid and is then reused.

18. The process of claim 1, wherein the furfural product obtained upon dehydration is subjected to a purification process to obtain pure furfural.

19. The process of claim 18, wherein the furfural product obtained from said dehydration step is purified by distillation by the application of a vacuum on the order of 0.1 to 0.3 bars absolute at a temperature up to about 100°–110° C.

* * * * *